(12) United States Patent
Takeuchi et al.

(10) Patent No.: US 6,566,394 B1
(45) Date of Patent: May 20, 2003

(54) SALICYLAMIDE DERIVATIVES

(75) Inventors: Tomio Takeuchi, Tokyo (JP); Kazuo Umezawa, Tokyo (JP); Sakino To-E, Chiba (JP); Naoki Matsumoto, Yokohama (JP); Tsutomu Sawa, Ayase (JP); Takeo Yoshioka, Ayase (JP); Naoki Agata, Fujisawa (JP); Shin-ichi Hirano, Chigasaki (JP); Kunio Isshiki, Zama (JP)

(73) Assignees: Mercian Corporation, Tokyo (JP); Zaidan Hojin Biseibutsu Kagaku Kenkyu Kai, Tokyo (JP)

( * ) Notice: Subject to any disclaimer, the term of this patent is extended or adjusted under 35 U.S.C. 154(b) by 0 days.

(21) Appl. No.: 10/049,158
(22) PCT Filed: Aug. 9, 2000
(86) PCT No.: PCT/JP00/05332
§ 371 (c)(1),
(2), (4) Date: May 30, 2002
(87) PCT Pub. No.: WO01/12588
PCT Pub. Date: Feb. 22, 2001

(30) Foreign Application Priority Data

Aug. 11, 1999 (JP) .......................................... 11/227389

(51) Int. Cl.[7] .................... A61K 31/336; A61K 31/609; C07D 303/06; C07D 303/36; C07D 237/38
(52) U.S. Cl. ........................ 514/475; 514/546; 514/563; 549/546; 560/142; 560/143; 564/169; 564/176; 564/177
(58) Field of Search ................................ 514/475, 546, 514/563; 549/546; 560/142, 143; 564/169, 176, 177

(56) References Cited

PUBLICATIONS

Matsumoto et al., Bioorg. Med. Chem. Lett. , 2000, vol. 10, No. 9, pp. 865–869.*
Taylor et al., Synthesis, May 1998, pp. 775–790.*

* cited by examiner

Primary Examiner—Ba K. Trinh
(74) Attorney, Agent, or Firm—Finnegan, Henderson, Farabow, Garrett & Dunner, L.L.P.

(57) ABSTRACT

Salicylamide derivatives represented by formulae (1a) and (1b); intermediates in the production thereof; a process for producing the same; and drugs containing the same as the active ingredient. The salicylamide derivatives represented by formulae (1a) and (1b) are useful as anti-inflammatory agents and immunosuppressive agents which exert an effect of inhibiting the activation of NF-κB with little side effects.

17 Claims, 2 Drawing Sheets

SALICYLAMIDE DERIVATIVES

This application is a 371 of PCT/JP00/05332 dated Aug. 9, 2000.

TECHNICAL FIELD

The present invention relates to novel salicylamide derivatives, to a process for producing the same and to drugs containing the same as the active ingredient. More particularly, the present invention relates to novel salicylamide derivatives exerting an effect of inhibiting the activation of NF-κB and useful as anti-inflammatory agents and immunosuppressive agents, to intermediates in the production thereof, to a process for producing the same, and to drugs containing the salicylamide derivatives or salts thereof as the active ingredient.

BACKGROUND ART

Anti-inflammatory agents conventionally used include steroid agents, prostaglandin synthesis inhibitors and so forth. Also, cyclosporin, FK506 (tacrolimus) and so forth have been used as immunosuppressive agents. However, it has been pointed out that these drugs have problems in effects and side effects.

In particular, generally many of them have strong side effects, which is a severe limit upon their use as anti-inflammatory agents and immunosuppressive agents.

Accordingly, it has been desired to discover or create novel drugs exerting little side effects and having novel chemical structures and operating mechanisms, so that there have been made studies for discovering or creating novel compounds that have different chemical structures and operating mechanisms from those of conventionally used drugs and exhibiting excellent anti-inflammatory activity or immunosuppressing activity.

NF-κB was identified as a nucleoprotein bonded to the enhancer of immunoglobulin κ-chain gene (Cell 46, 705–716, 1986) and at first it was considered to be a transcription factor specific to B cells but afterwards it revealed that it exists in various types of cells. NF-κB is a hetero dimer consisting of two subunits and is constituted by various combinations of p50 or p52 having Rel homology domain (RHD) of about 300 amino acids with RelA, c-Rel or RelB (Annu. Rev. Immunol., 14, 649–681, 1996).

NF-κB is a dominant transcription factor in biophylaxis reaction and genes induced by NF-κB includes besides immunoglobulin, cytokines (IL-1, IL-2, IL-6, IL-8, TNF, etc.), cell adhesion factors (E-selectin, ICAM-1, VCAM-1, etc.), nitrogen oxide (NO) synthetase, Fas ligand, etc., most of which are deeply concerned in immune response or inflammatory reaction (Cell, 87, 13–20, 1996).

Factors known to cause activation of NF-κB include besides TNF-α, IL-1, antigen stimulation, TPA, UV, activated oxygen (Annu. Rev. Immunol., 12, 141–179, 1994). Therefore, it is conceived that stimulation of cells with TNF-α or the like and discovery of a low molecular weight substance induced by the stimulation that inhibits activation of NF-κB will undergo further development of anti-inflammatory agents and immunosuppressive agents.

DISCLOSURE OF INVENTION

In consideration of the above problems, the present inventors have repeated screening extensively and as a result they have found that novel salicylamide derivatives having specified chemical structures, i.e., compounds represented by the formula (1a) (DHM2EQ) and the compounds represented by the formula (1b) (DHM3EQ) described hereinbelow exert an effect of inhibiting the activation of NF-κB, thereby achieving the present invention.

That is, the present invention provides the following novel salicylamide derivatives, a process for producing the same, and drugs containing the same as the active ingredient.

[1] Salicylamide derivatives represented by formula (1)

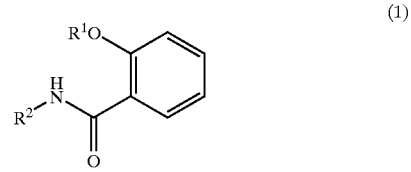

(1)

wherein $R^1$ represents a hydrogen atom or a C2–4 alkanoyl group, $R^2$ represents a group represented by the following formulae (A), (B), (C), (D), (E), (F) or (G):

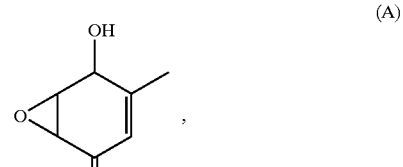

(A)

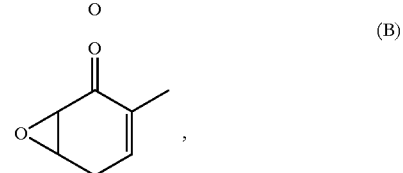

(B)

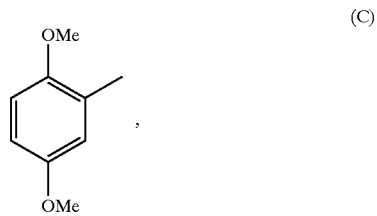

(C)

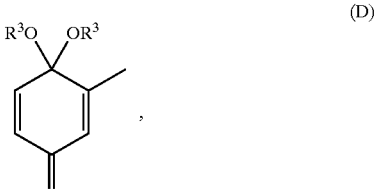

(D)

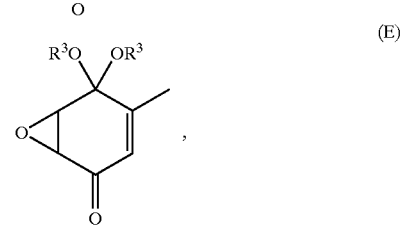

(E)

(F) 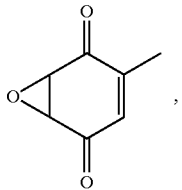

(G) 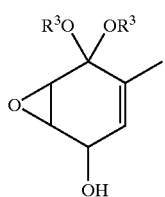

Wherein R³ represents a C1–4 alkyl group.

[2] Salicylamide derivatives as described in [1] above represented by formulae (1a) or (1b)

(1a) 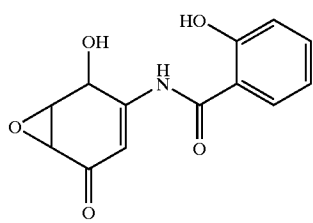 or (1b) 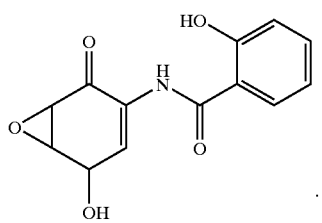

[3] Salicylamide derivatives as described in [1] above, represented by formula (2)

(2) 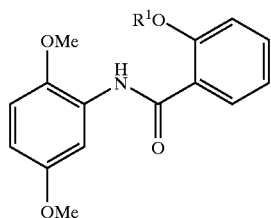

wherein the symbol in the formula has the same meaning as described in [1] above.

[4] Salicylamide derivatives as described in [1] above, represented by formula (3)

(3) 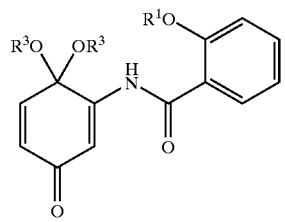

wherein the symbols in the formula have the same meanings as described in [1] above.

[5] Salicylamide derivatives as described in [1] above, represented by formula (4)

(4) 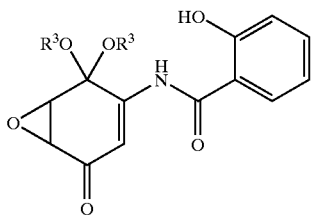

wherein the symbol in the formula has the same meaning as described in [1] above.

[6] A salicylamide derivative as described in [1] above, represented by formula (5)

(5) 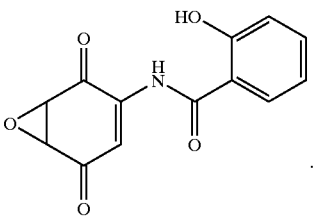

[7] Salicylamide derivatives as described in [1] above, represented by formula (6)

(6) 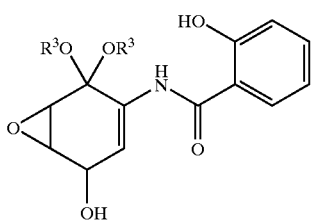

wherein the symbol in the formula has the same meaning as described in [1] above.

[8] A process for producing salicylamide derivatives represented by formula (2)

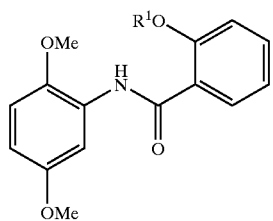

(2)

wherein the symbol in the formula has the same meaning as in described above, comprising reacting 2,5-dimethoxyaniline with O-alkanoylsalicyloyl halide represented by formula (7)

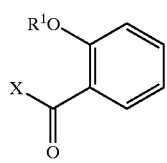

(7)

wherein $R^1$ has the same meaning as described in [1] above, and X represents a halogen atom.

[9] A process for producing salicylamide derivatives represented by formula (3)

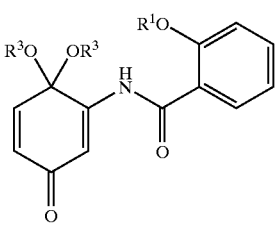

(3)

wherein the symbols in the formula have the same meanings as described above, comprising reacting a salicylamide derivative represented by formula (2)

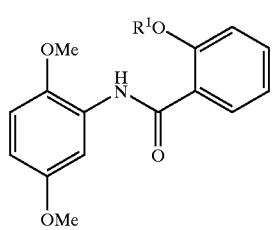

(2)

wherein the symbol in the formula has the same meaning as in [1] above, with an alkanol represented by formula $R_3OH$ wherein $R^3$ is a C1–4 alkyl group, in the presence of a compound represented by a formula $C_6H_3I(OAc)_2$ wherein Ac is an acetyl group.

[10] A process for producing salicylamide derivatives represented by formula (4)

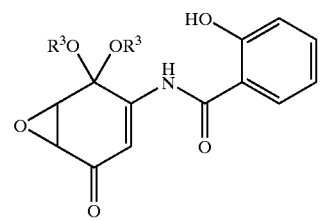

(4)

wherein the symbol in the formula has the same meaning as described above, comprising subjecting a salicylamide derivative represented by formula (3)

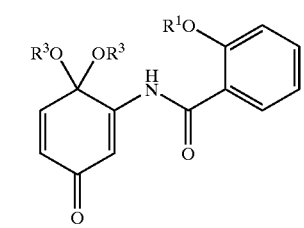

(3)

wherein the symbols in the formula have the same meanings as in [1] above, to epoxidation.

[11] A process for producing a salicylamide derivative represented by formula (5)

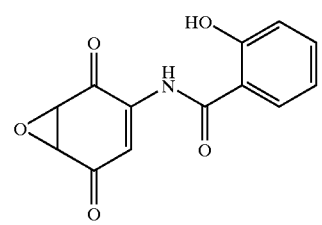

(5)

comprising subjecting a salicylamide derivative represented by formula (4)

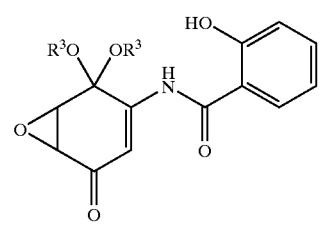

(4)

wherein the symbols in the formula have the same meanings as described in [1] above, to dedialkylketalation.

[12] A process for producing salicylamide derivatives represented by formula (6)

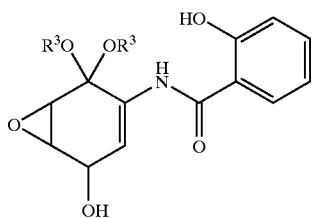

(6)

wherein the symbol in the formula has the same meaning as described above, comprising subjecting a salicylamide derivatives represented by formula (4)

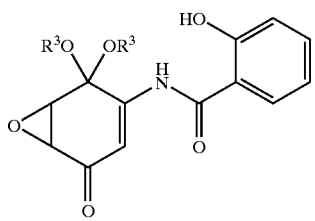

(4)

wherein the symbols in the formula have the same meanings as in [1] above, to reduction.

[13] A process for producing a salicylamide derivative represented by formula (1a)

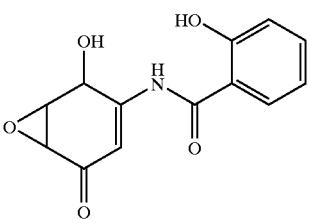

(1a)

comprising subjecting a salicylamide derivative represented by formula (5)

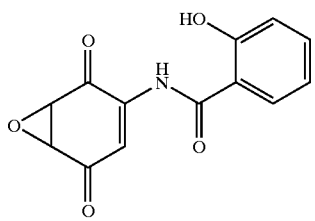

(5)

to reduction.

[14] A process for producing a salicylamide derivative represented by formula (1b)

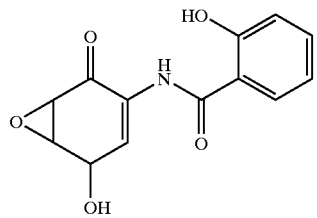

(1b)

comprising subjecting a salicylamide derivative represented by formula (6)

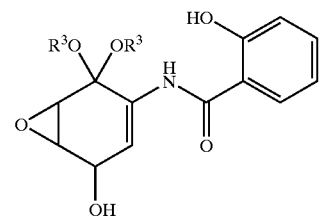

(6)

wherein the symbol in the formula has the same meaning as described in [1] above, to dedialkylketalation.

[15] A drug comprising a salicylamide derivative represented by formulae (1a) or (1b) as described in [2] above or a salt thereof as the active ingredient.

[16] An agent for inhibiting the activation of NF-κB comprising a salicylamide derivative represented by formulae (1a) or (1b) as described in [2] above or a salt thereof as the active ingredient.

[17] Anti-inflammatory agent or immunosuppressive agent, comprising a salicylamide derivative represented by formulae (1a) or (1b) as described in [2] above or a salt thereof as the active ingredient.

DETAILED DESCRIPTION OF THE INVENTION

Figure 1A:
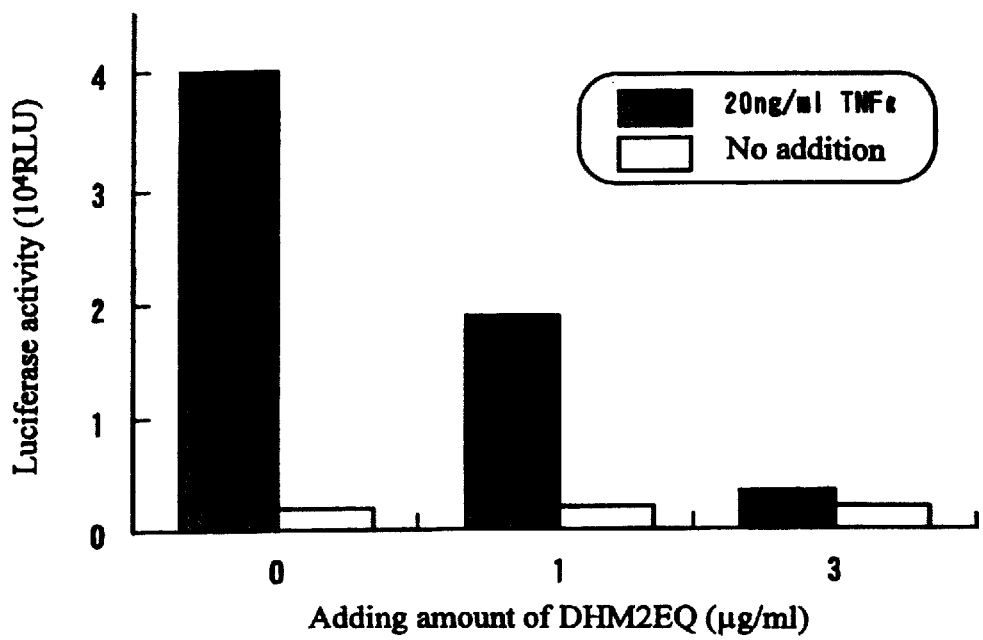
FIGS. 1(A) and 1(B) are graphs illustrating NF-κB production inhibitory activities of DHM2EQ and DHM3EQ, respectively.

The C1–4 alkyl group represented by $R^3$ in $R^2$ in the formula (1) above includes methyl, ethyl, propyl, butyl groups and isomer groups thereof, with a methyl group and an ethyl group being preferred.

The C2–4 alkanoyl groups represented by $R^1$ in the formula (2) and (3) above, include acetyl, propionyl and butanoyl groups and isomer groups thereof with an acetyl group being preferred.

The halogen group represented by X in the formula (7) above includes fluorine, chlorine, bromine and iodine atoms, with chlorine and bromine atoms being preferred.

[Process for Producing the Compounds of the Present Invention]

The compounds (salicylamide derivatives) of the present invention can be produced according to the synthetic process by Wipf et al. (Synthesis, No. 12, p. 1549–1561, 1995).

Next, the process for producing the compounds of the present invention will be illustrated based on the following reaction schemes.

In the following steps, the compounds represented by the formulae (1a) and (1b) and production intermediate compounds represented by the formulae (2) to (6) are novel compounds.

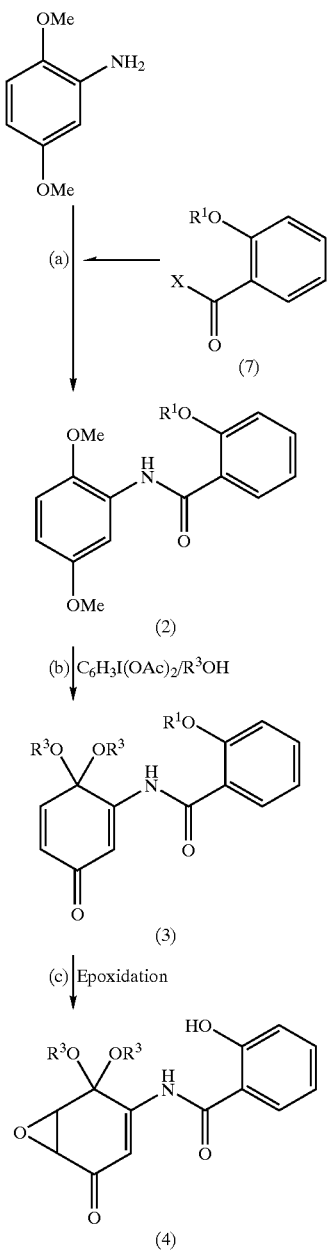

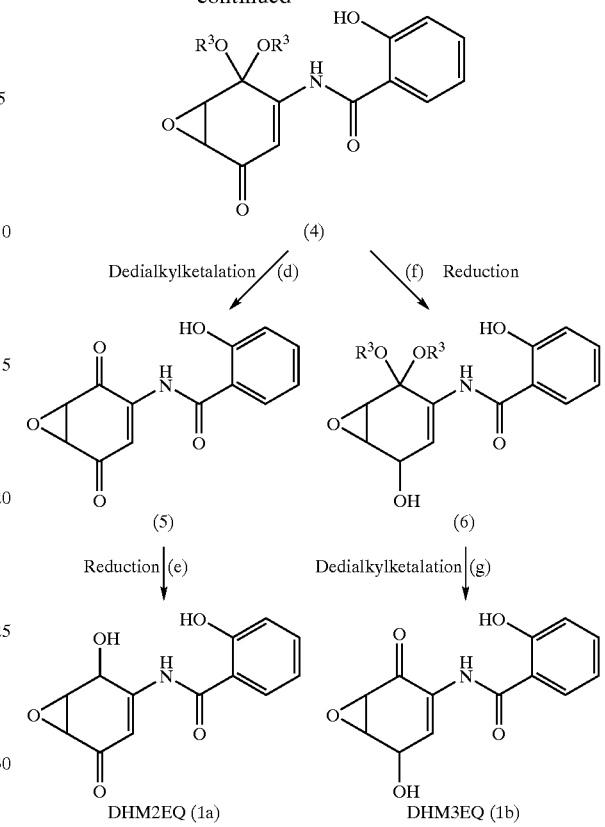

Step a: Preparation of N-(2-alkanoylbenzoyl)-2,5-dimethoxyaniline 2,5-Dimethoxyaniline is dissolved in a solvent (pyridine, etc.), and ethyl acetate solution of O-alkanoylsalicyloyl halide is added thereto at −78° C. to 50° C., preferably under ice cooling, and the mixture is allowed to react under stirring. After stopping the reaction by addition of water, ethyl acetate is added to the reaction mixture, which then is sequentially washed with hydrochloric acid, water, a sodium hydrogencarbonate solution and water. After drying, the organic layer is concentrated under reduced pressure and dried under vacuum to obtain an N-(2-alkanoylbenzoyl)-2, 5-dimethoxyaniline compound represented by formula (2). The compound can be used in the next step without purification.

Step b: Preparation of 3-(O-alkanoylsalicyloyl) amino-4,4-dialkoxy-2,5-cyclohexadienone The compound of formula (2) obtained as described above is dissolved in a solvent such as methanol, diacetoxy-iodobenzene is added thereto at −20° C. to 50° C., preferably under ice cooling and the mixture is allowed to react at room temperature under stirring. After concentration under reduced pressure, ethyl acetate is added and the reaction mixture is washed with sodium hydrogencarbonate solution and saline. Then, the solvent is concentrated under reduced pressure and the obtained residue is purified by column chromatography to obtain 3-(O-alkanoylsalicyloyl)amino-4, 4-dialkoxy-2,5-cyclohexadienone.

Step c: Preparation of 5,6-epxoy-4,4-dialkoxy-3-salicyloylamino-2-cyclohexenone compound 3-(O-Alkanoylsalicyloyl)amino-4,4-dialkoxy-2,5-cyclohexadienone represented by formula (3) is dissolved in a solvent (tetrahydrofuran, methanol, etc.), hydrogen peroxide water and sodium hydroxide are added thereto at −20° C. to 50° C., preferably under ice cooling, and the mixture is allowed to react while stirring. Ethyl acetate is added to the reaction mixture, which is sequentially washed with hydrochloric solution, aqueous sodium thiosulfate solution, and saline. After drying, the reaction mixture is dried under vacuum. In order to remove the residual starting compound, the residue is dissolved in acetone, p-toluenesulfonic acid is added thereto and stirred at room temperature to decompose the starting compound. Ethyl acetate is added to the residue obtained by distilling off methanol under reduced pressure, and the solution is washed with water. The residue obtained by drying the ethyl acetate layer is purified by column chromatography to obtain 5,6-epxoy-4,4-dialkoxy-3-salicyloylamino-2-cyclohexenone compound represented by formula (4).

Step d: Preparation of 5,6-epoxy-2-salicyloylamino-2cyclohexen-1,4dione 5,6-Epxoy-4,4-dialkoxy-3-salicyloylamino-2-cyclohexenone compound represented by formula (4) is dissolved in methylene chloride, an inorganic acid or organic acid (trifluoroboron diethyl ether complex, etc.) is added under ice cooling, and the mixture is allowed to react while stirring. A solvent (ethyl acetate, etc.) is added to the reaction mixture, which is washed with water. After concentrating the ethyl acetate layer, the obtained residue is washed with methanol to obtain 5,6-epoxy-2-salicyloylamino-2-cyclohexen-1,4-dione represented by formula (5).

Step e: Preparation of 5,6-epoxy-4-hydroxy-3-salicyloylamino-2-cyclohexenone (DHM2EQ)

5,6-Epoxy-2-salicyloyalamino-2-cyclohexen-1,4-dione represented by formula (5) is suspended in a solvent (methanol, ethanol, THF, etc.) and a reducing agent (sodium borohydride, etc.) is added thereto at −78° C. to 50° C., preferably under ice cooling. A solvent (ethyl acetate, methylene chloride, etc.) is added to the reaction mixture, which is sequentially washed with hydrochloric acid and water. After drying, the solvent layer is concentrated under reduced pressure, suspended, stirred and washed with methanol to obtain 5,6-epoxy-4-hydroxy-3-salicyloylamino-2-cyclohexenone (DHM2EQ) represented by formula (1a).

Step f: Preparation of 3,3-dialkoxy-4,5-epoxy-6-hydroxy-2-salicyloylamino-cyclohexene 5,6-Epxoy-4,4-dialkoxy-3-salicyloylamino-2-cyclohexenone compound represented by formula (4) is dissolved in a mixed solution of a solvent such as methanol and sodium hydrogen carbonate solution, a reducing agent (sodium borohydride, etc.) is added at −78° C. to 50° C., preferably under ice cooling, and the mixture is allowed to react while stirring. A solvent (ethyl acetate, etc.) is added to the reaction mixture, which is washed with hydrochloric acid and water. After drying, the solvent layer is concentrated under reduced pressure, dried under vacuum and purified by column chromatography to obtain 3,3-dialkoxy-4,5-epoxy-6-hydroxy-2-salicyloylamide-cyclohexene represented by formula (6)

Step g: Preparation of 5,6-epoxy-4-hydroxy-2-salicyloylamino-2-cyclohexenone (DHM3EQ)

3,3-Dialkoxy-4,5-epoxy-6-hydroxy-2-salicyloylamino-cyclohexene represented by formula (6) is dissolved in a solvent (acetone, etc), p-toluenesulfonic acid is added to the solution, which then is stirred at room temperature to proceed reaction. A solvent (ethyl acetate, etc.) is added to the reaction mixture, which is washed with water. The solvent layer is dried, concentrated under reduced pressure and purified to obtain 5,6-epoxy-4-hydroxy-2-salicyloylamino-2-cyclohexenone (DHM3EQ) represented by formula (1b).

[Pharmacological Activity]

The biological activity of the compounds of the present invention was confirmed on DHM2EQ and DHM3EQ by the following tests.

A) NF-κB Production Inhibitory Activity

The NF-κB production inhibitory activity was measured by luciferase reporter gene assay as shown below.

[Luciferase Reporter Gene Assay]

A reporter using luciferase DNA was prepared and the NF-κB production inhibitory activity was measured by use of promoter/reporter assay.

1) Plasmid

As the plasmid for luciferase assay, 3×κBTK-Luc (endowed by Dr. Junichiro INOUE of The Institute of Medical Science, The University of Tokyo) obtained by coupling luciferase gene derived from lampyrid to 3×κB derived from Igκ gene and HSV-TK promoter was used. Further, for the β-galactosidase assay, a plasmid obtained by coupling β-galactosidase gene to β-actin promoter (endowed by Dr. Junichiro INOUE of The Institute of Medical Science, The University of Tokyo) was used.

2) Transfection and Luciferase Assay

Transfection was performed by a DEAE-dextran method. $2×10^6$ cell were washed once with 1×TBS (Tris-HCL (25 mM), NaCl (137 mM), KCl (5 mM), and $Na_2HPO_4$ (0.5 mM)) and incubated in transfection buffer (2×TBS (200 μl), 100×$Ca^{2+}$.$Mg^{2+}$ (($CaCl_2$.$2H_2O$) (78 mM, 4 μl), $MgCl_2$.$6H_2O$ (76 mM)), and DEAE-dextran (1 mg/ml, 200 μl)) containing 1 μg of plasmid at room temperature for 30 minutes with tapping for every 10 minutes. Thereafter, the cells were washed with 1×TBS and inoculated at 37° C. on a 12-well plate (Coster: N.Y., U.S.A.) at $1×10^6$ cells/well. On the day next, DHM2EQ or DHM3EQ solutions in various concentrations were added. After 2 hours' incubation, TNF-α (20 ng/ml) was further added and incubation was performed for 6 hours. The cells were centrifuged at 3,500 rpm for 5 minutes. After removing the supernatant, 50 μl each of lysis buffer (Tris-HCl (25 mM, pH 7.8), DTT (2 mM), 1,2-diaminocyclohexane-N,N',N',N-tetraacetic acid (2 mM), and 10% glycerol, 1% Triton X-100) was added and the cells were solubilized in ice for 30 minutes. Then this was centrifuged at 15,000 rpm for 5 minutes and the supernatant was used as a sample.

For 10 μl of the sample, 100 μl of a luminescent substrate solution (Tricine (20 mM), $(MgCO_3)$.$4Mg(OH)_2$.$5H_2O$ (1.07 mM), $MgSO_4$ (2.67 mM), EDTA (0.1 mM), DTT (33.3 mM), Coenzyme A (270 μM), luciferin (470 μM), and ATP (530 μM)) was added and amount of luminescence was quantitated by use of Lumat LB9501 (Berthold: Bad Wildbad, Germany). Further, the measured amounts were corrected by β-galactosidase assay to obtain the value of luciferase activity.

3) β-Galactosidase Assay

β-Galactosidase DNA was to measure transfection efficiency and effect normalization.

20 μl of a sample was added to 230 μl of Z buffer (KCl (10 mM), $MgSO_4$ (1 mM), 2-mercaptoethanol (50 mM), and $NaPO_4$ (100 mM: pH 7.5)) and further 50 μl of o-nitrophenyl-β-D-galactopyranoside (ONPG, Sigma) and a NaPO$_4$ (100 mM, pH 7.5) solution (2 mg/ml) were added and the mixture was incubated at 37° C. When the solution turned yellow, 250 µl of Na$_2$CO$_3$ (1 M) was added thereto and the optical density at absorption wavelength of 420 nm was measured by use of a spectrophotometer (Hitachi, Ltd.)

B) Collagen-induced Arthritis Preventing Effect

Type II collagen was emulsified together with an equivalent volume of Freund's complete adjuvant to prepare 1.5 mg/ml of administration solution. This was intradermally inoculated to the radicular portion of mouse tail in an amount of 0.1 ml (150 µg/mouse) to sensitize the mouse. After 3 weeks, 0.1 ml of type II collagen emulsified in the same operational manner as described was intraperitoneally administered to mouse (150 µg/mouse) to effect booster immunization to induce arthritis.

Figure 2A:
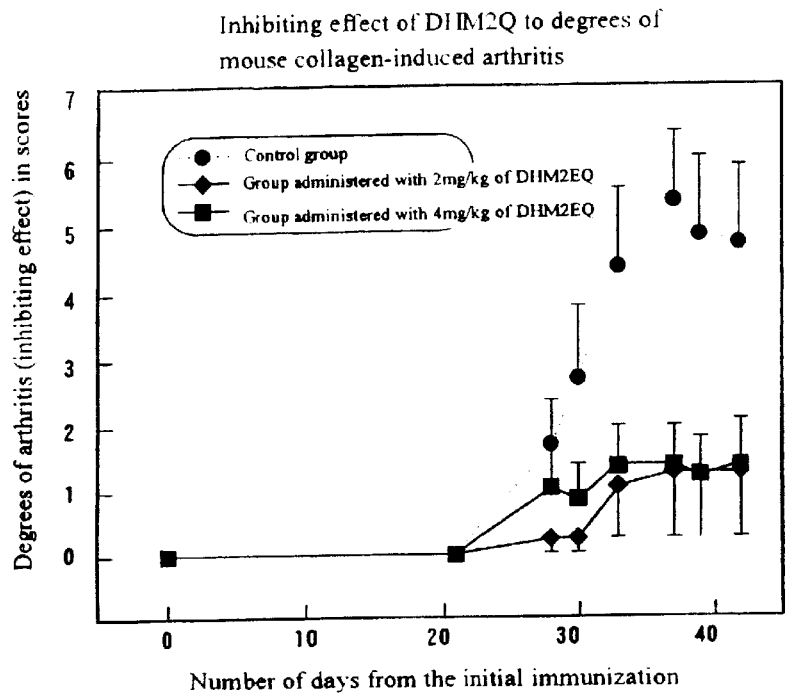
FIGS. 2(A) and 2(B) are graphs illustrating effects of DHM2EQ and DHM3EQ, respectively, on mouse collagen-induced arthritis.
Figure 2B:
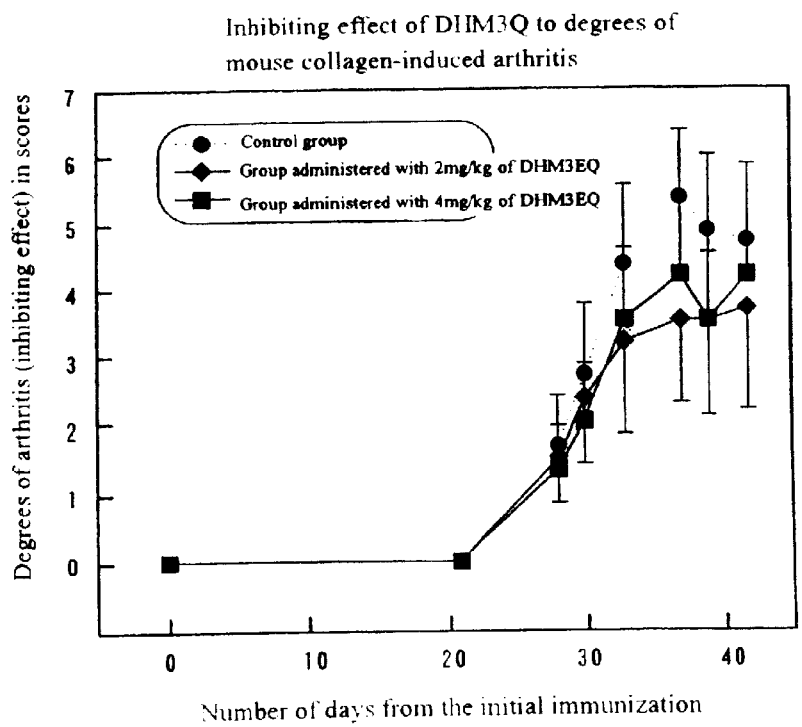

6 Animals/group of mice were intraperitoneally administered with DHM2EQ and DHM3EQ in a dosage of 2 mg/kg or 4 mg/kg 3 times/week from the day of initial immunization in a ratio of 0.1 ml/10 g of the bodyweight, in total 18 times/6 weeks. The control group (6 animals/group) was administered with 0.5% CMC solution in the same schedule as described above and to provide normal group (4 animals/group) in which no collagen arthritis was induced. The effect of inhibiting collagen-induced arthritis was evaluated by degrees of the flare, swelling and stiffening of anterior limb and posterior limb in scores of 0 to 4 (the maximum score of total for 4 limbs was 16). Score 0 was assigned to the case where no symptom was observed, score 1 was assigned to the case where only 1 of small joints such as fingers of the 4 limbs showed flare or swelling, score 2 was assigned to the case where 2 or more small joints or relatively large joints such as wrist or ankle of the 4 limbs showed flare or swelling, score 3 was assigned to the case where a whole hand or foot showed flare or swelling, and score 4 was assigned to the case where it was judged that the swelling of one hand or foot reached maximum with stiffening of the joint. The results obtained are shown in FIGS. 2(A) and 2(B).

Figure 1B:
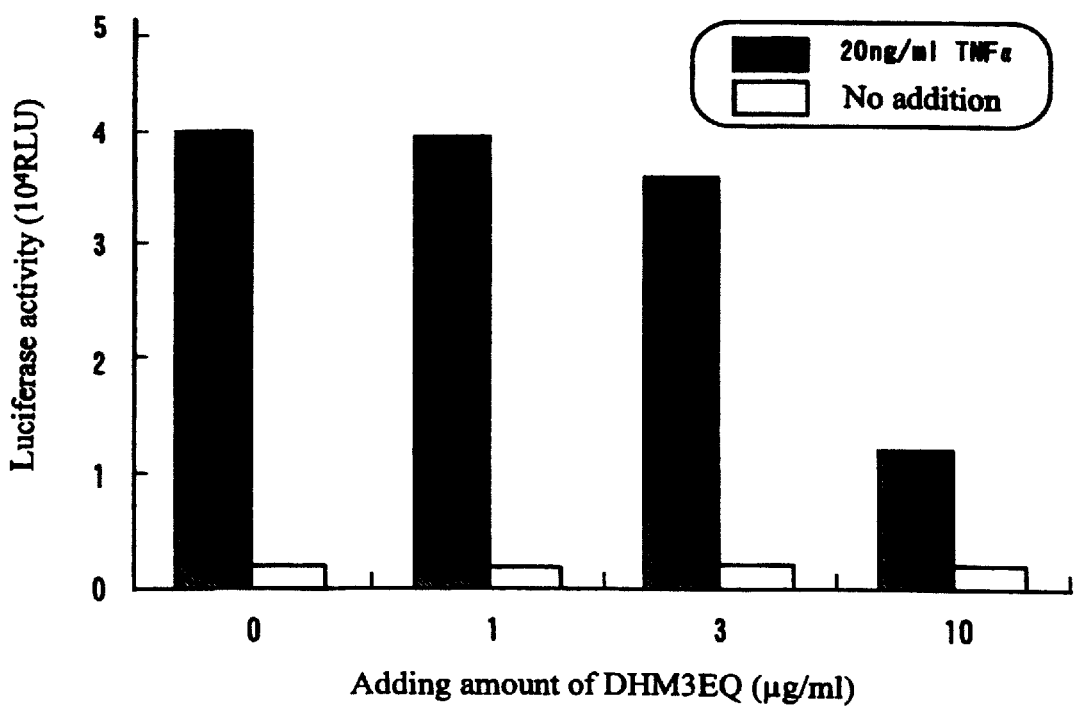

As will be apparent from the results shown in FIGS. 1(A) and 1(B), the novel compounds of the present invention inhibited NF-κB activity starting from 1 µg/ml in the case of DHM2EQ (FIG. 1(A)) and at 10 µg/ml in the case of DHM3EQ (FIG. 1(B)). Furthermore, as will be apparent form FIGS. 2(A) and 2(B), DHM2EQ and DHM3EQ, in particular DHM2EQ, inhibited collagen-induced arthritis, i.e., an animal experiment model of chronic articular rheumatism by use of mice and thus their in vivo effectiveness was demonstrated.

Industrial Applicability

[Application as a Drug]

As described above, DHM2EQ and DHM3EQ, the compounds of the present invention exhibited NF-κB activation inhibitory effect and in vivo preventing effect for collagen-induced arthritis. Therefore, the compounds represented by formulae (1a) or (1b) are conceived to be useful as anti-inflammatory agents and immunosuppressive agents.

The compounds represented by formulae (1a) or (1b) are weakly acidic substances and their salts include salts with organic bases such as quaternary ammonium salt, or salts with various metals, for example salts with alkali metals such as sodium. They may be used in the form of such salts.

The compounds represented by formulae (1a) or (1b) and salts thereof can be administered after they are prepared into solid compositions or liquid compositions for oral administration, injections for parenteral administration, external preparations, suppositories and so forth. The dosage may vary depending on age, body weight, symptom, therapeutic effect, method of administration, treating time and so forth but usually, they are administered in an amount of about 1 mg to 100 mg per day for an adult in 1 time or divided into several times.

The solid composition for oral administration includes tablets, pills, capsules, powder, granules and so forth. The composition may contain in addition to inert diluents, various additives, for example, lubricants, disintegrators, or dissolution aids according to a conventional method. The tablets or pills may be covered with a film of a gastric or enteric dissolving substance as needed.

The liquid substance for oral administration includes emulsions, solutions, syrup, elixirs and so forth that are pharmaceutically acceptable. The composition may contain in addition to inert diluents various auxiliaries such as humectants, suspending agents, edulcorants, flavors, fragrants, and preservatives.

The injection for parenteral administration according to the present invention includes sterile aqueous or nonaqueous solvents, suspending agents and emulsifiers. The injection may further contain auxiliaries such as preservatives, humectants, emulsifiers, dispersants, stabilizers, dissolution aids (for example glutamic acid or aspartic acid).

The composition for parenteral administration includes external liquid agents, ointments, liniments, suppositories for rectal administration, and so forth.

BEST MODE FOR CARRYING OUT THE INVENTION

Hereinafter, the present invention will be illustrated in more detail by way of examples. However, the present invention is not limited thereto.

EXAMPLE 1

Synthesis of N-(2-acetoxybenzoyl)-2,5-dimethoxyaniline 2,5-Dimethoxyaniline (10.0 g, 65.3 mmol) was dissolved in pyridine (100 ml), and a solution of O-acetylsalicyloyl chloride (13.0 g, 65.3 mmol) in ethyl acetate (50 ml) was added thereto over 15 minutes under ice cooling. Thereafter, the mixture was stirred for 15 minutes at the same temperature as above. After adding water (10 ml) to the reaction mixture to stop the reaction, ethyl acetate (500 ml) was added and the reaction mixture was washed with 3 N hydrochloric acid (500 ml), water (500 ml), 2% sodium hydrogen carbonate solution (500 ml), and water (500 ml) in order. After drying it over Glauber's salt, the ethyl acetate layer was concentrated under reduced pressure and dried under vacuum to obtain the titled compound (19.8 g) as pale yellow syrup. The compound was used in the subsequent step without purification. The titled compound purified by preparative thin layer chromatography had the following physical properties.

Infrared Absorption Spectra: νmax (KBr) 3409, 1773, 1671, 1603, 1535, 1478, 1283, 1221, 1179 cm$^{-1}$, Ultraviolet Absorption spectra: λmax (MeOH) nm (ε) 224 (18100), 309 (7890), FAB mass spectrum (m/z): 316 (M+H)$^+$, $^1$H-NMR spectra (CDCl$_3$, 400 MHz): δ2.37 (3H, s), 3.82 (3H, s), 3.87 (3H, s), 6.62 (1H, dd, J=2.8 and 8.8 Hz), 6.84 (1H, d, J=8.8 Hz), 7.17 (1H, d, J=7.2 Hz), 7.37 (1H, t, J=8.0 Hz), 7.52 (1H, dt, J=2.0 and 7.2 Hz), 7.99 (1H, dd, J=2.0 and 8.0 Hz), 8.31 (1H, d, J=2.8 Hz), 8.93 (1H, br s).

EXAMPLE 2

Synthesis of 3-(O-acetylsalicyloyl)amino-4,4-dimethoxy-2,5-cyclohexadienone

N-(2-acetoxybenzoyl)-2,5-dimethoxyaniline (19.8 g) obtained in Example 1 was dissolved in methanol (400 ml)

and diacetoxyiodobenzene (27.3 g, 84.9 mmol) was added thereto under ice cooling and the mixture was stirred at room temperature for 1 hours. The reaction mixture was concentrated under reduced pressure to obtain brown syrup-like residue, to which was added ethyl acetate (1 1). The mixture was washed with 5% sodium hydrogen carbonate solution (1 l), and 10% saline (1 l). The ethyl acetate layer was concentrated under reduced pressure to obtain brown syrup-like residue, which was purified by silica gel chromatography (1 kg, hexane/ethyl acetate=2/1) to obtain 12.8 g of solids. They were suspended in 30 ml of methanol and stirred to purify them. Thus, 10. 9 g of the titled compound was obtained as white solids (yield: 50% in two steps).

Melting point: 150–152° C.

Infrared Absorption Spectra: νmax (KBr) 3451, 1769, 1694, 1520. 1198 cm$^{-1}$,

Ultraviolet Absorption Spectra: λmax (MeOH) nm (ε) 238 (14200), 313 (13800),

FAB mass spectrum (m/z): 332 (M+H)$^+$, $^1$H-NMR spectra (CDCl$_3$, 400 MHz): δ2.47 (3H, s), 3.31 (6H, s), 6.48 (1H, dd, J=2.0 and 10.8 Hz), 6.61 (1H, d, J=10.8 Hz),7.20 (1H, d, J=7.2 Hz), 7.39 (1H, t, J=7.6 Hz), 7.57 (2H, overlapped),8.05 (1H, dd, J=1.6 and 7.6 Hz), 8.89 (1H, br s).

EXAMPLE 3

Synthesis of 5,6-epoxy-4,4-dimethoxy-3-salicyloylamino-2-cyclohexenone 3-(O-Acetylsalicyloyl)amino-4,4-dimethoxy-2,5-cyclohexadienone (10.9 g, 33.0 mmol) was dissolved in tetrahydrofuran (200 ml), 30% hydrogen peroxide (60 ml) and 1N sodium hydroxide (165 ml) were added thereto under ice cooling, and the mixture was stirred for 2 hours at the same temperature as described above. While the starting compound remained, treatment of the reaction mixture was performed, since according as the reaction was continued, decomposition of the objective compound occurred. Ethyl acetate (500 ml) was added and the reaction mixture was washed with 1N hydrochloric acid (300 ml), aqueous 10% sodium thiosulfate solution (300 ml×2), and 10% saline (300 ml) in order. After drying it over Glauber's salt, the ethyl acetate layer was dried under vacuum to obtain pale yellow syrup-like residue. In order to facilitate removal of the starting compound having a spot close to the objective compound on TLC, the residue was dissolved in acetone (100 ml), p-toluenesulfonic acid was added, and stirred at room temperature for 1.5 hours to decompose the starting compound. Methanol was distilled off under reduced pressure to obtain residue, to which was added ethyl acetate (200 ml) and the mixture was washed with water (200 ml). The ethyl acetate layer was dried over Glauber's salt to obtain deep brown syrup, which was purified by silica gel column chromatography (400 g, toluene/ethyl acetate=1/1) to obtain 6.58 g of yellow solids. The solids were suspended in methanol (20 ml) and stirred to wash to obtain 5.34 g of the titled compound as white solids (yield: 53%).

Melting point: 147–149° C.,

Infrared Absorption Spectra: νmax (KBr) 3265, 1674, 1651, 1530, 1236, 1119, 1053 cm$^{-1}$, Ultraviolet Absorption Spectra: λmax (MeOH) nm (ε) 242 (5100), 314 (19600), FAB Mass Spectrum (m/z): 306 (M=H)$^+$, $^1$H-NMR spectra (CDCl$_3$, 400 MHz): δ3.35 (3H, s), 3.58 (1H, dd, J=2.4 and 4.4 Hz), 3.75 (3H, s), 3.89 (1H, d, J=4.4 Hz), 6.94 (1H, t, J=8.4 Hz), 7.04 (1H, dd, J=0.8 and 8.4 Hz), 7.24 (1H, d, J=2.4 Hz), 7.38 (1H, dd, J=1.2 and 8.4 Hz), 7.49 (1H, br t, J=8.4Hz), 8.65 (1H, br s), 11.37 (1H, s).

EXAMPLE 4

Synthesis of 5,6-epoxy-2-salicyloylamino-2-cyclohexen-1,4-dione 5,6-Epoxy-4,4-dimethoxy-3-salicyloylamino-2-cyclohexenone (1.0 g, 3.27 mmol) was dissolved in methylene chloride (25 ml), trifluoroboron diethyl ether complex (1 ml) was added thereto under ice cooling, and the mixture was stirred at the same temperature as described above for 30 minutes. Ethyl acetate (300 ml) was added to the reaction mixture and the reaction mixture was washed with water (200 ml). After drying it over Glauber's salt, the ethyl acetate layer was dried under vacuum to obtain brown solids, which were washed with methanol (5 ml) to obtain the titled compound (399 mg) as pale brown solids (yield: 47%).

Melting point: 210° C. (decomposed),

Infrared Absorption Spectra: νmax (KBr) 3453, 3202, 1713, 1667, 1642, 1611, 1537, 1231 cm$^{-1}$, Ultraviolet Absorption Spectra: λmax (MeOH) nm (ε) 250 (11900), 326 (15000), FAB Mass Spectrum (m/z): 259 (M$^-$), $^1$H-NMR Spectra (acetone-d$_6$, 400 MHz): δ3.91 (1H, dd, J=2.4 and 4.0 Hz),4.11 (1H, d, J=4.0 Hz), 7.07 (1H, t, J=8.4 Hz), 7.13 (1H, d, J=8.4 Hz), 7.51 (1H, dt, J=1.6 and 8.4 Hz), 7.61 (1H, d, J=2.4 Hz), 8.06 (1H, dd, J=1.6 and 8.4 Hz), 10.83 (1H, br s), 10.88 (1H, br s).

EXAMPLE 5

Synthesis of DHM2EQ 5,6-Epoxy-2-salicyloylamino-2-cyclohexen-1,4-dione (81.8 mg, 0.316 mmol) was suspended in methanol (10 ml), sodium borohydride (11.9 mg, 0.316 mmol) was added thereto under ice cooling, and the mixture was stirred at the same temperature as described above for 10 minutes. Ethyl acetate (50 ml) was added to the reaction mixture and the reaction mixture was washed with 1N hydrochloric acid (50 ml) and water (50 ml) in order. After drying it over Glauber's salt, the ethyl acetate layer was dried under vacuum to obtain pale brown solids, which were suspended in with methanol (1 ml) and stirred to wash them to obtain DHM2EQ (45.3 mg) as white solids (yield: 72%).

Appearance and Property: White powder, weakly acidic substance,

Melting point: 185° C. (decomposed),

Rf value of TLC: 0.45 (measured after development by thin layer chromatography silica gel (Art. 1.05715, produced by Merck, Inc.) with chloroform-methanol (10:1) as a development solvent, Infrared Absorption Spectra: νmax (KBr) 3360, 1663, 1634, 1609, 1526, 1204, 1071 cm$^{-1}$, Ultraviolet Absorption Spectra: λmax (MeOH) nm (ε) 242 (5950), 314 (20400), FAB Mass Spectrum (m/z): 262 (M+H)$^+$, Molecular formula: $C_{13}H_{11}NO_5$, $^1$H-NMR Spectra (DMSO-d$_6$, 400 MHz): δ3.43 (1H, dd, J=2.4 and 4.4 Hz), 3.85 (1H, dd, J=2.4 and 4.0 Hz), 4.83 (1H, br s), 6.70 (1H, br s), 6.99 (2H, overlapped), 7.45 (1H, t, J=8.8 Hz), 7.93 (1H, dd, J=2.0 and 8.8 Hz), 10.83 (1H, br s), 10.88 (1H, br s).

EXAMPLE 6

Synthesis of 3,3-dimethoxy-4,5-epoxy-6-hydroxy-2-salicyloylamino-cyclohexene 5,6-Epoxy-2-salicyloylamino-2-cyclohexen-1,4-dione (200 mg, 0.655 mmol) was dissolved in a mixed solution of methanol (5 ml) and 5% sodium hydrogen carbonate (5 ml), sodium borohydride (24.8 mg, 0.655 mmol) was added thereto under ice cooling, and the mixture was stirred at the same temperature as described above for 30 minutes. Ethyl acetate (50 ml) was added to the reaction mixture and the reaction mixture was washed with 1N hydrochloric acid (50 ml) and water (50 ml) in order. After drying it over Glauber's salt, the ethyl acetate layer was concentrated under reduced pressure and dried under vacuum to obtain syrup (206 mg), which were developed by preparative thin layer chromatography with a developing solution of toluene/acetone (1/1) to obtain the titled compound (97 mg) as a colorless, transparent syrup (Yield: 48 %).

Melting point: 170–172° C.,

Infrared Absorption Spectra: νmax (KBr) 3366, 3285, 1657, 1537, 1236, 1128, 1063, 1046 cm$^{-1}$, Ultraviolet Absorption Spectra: λmax (MeOH) nm (ε) 242 (8180), 262 (9190). 300 (7610), FAB Mass Spectrum (m/z): 308 (M+H)$^+$, $^1$H-NMR Spectra (CDCl$_3$, 400 MHz): δ2.13 (1H, d, J=10.0 Hz), 3.27 (3H, s), 3.49 (1H, s), 3.63 (1H, s), 3.64 (3H, s), 3.64 (1H, overlapped), 4.76 (1H, dd, J=2.0 and 10.0 Hz), 6.68 (1H, d, J=2.0 Hz), 6.89 (1H, t, J=7.6 Hz), 7.01 (1H, d, J=7.6 Hz), 7.34 (1H, dd, J=1.5 and 8.3 Hz), 7.43 (1H, t, J=7.6 Hz), 8.23 (1H, s), 11.87 (1H, s), $^1$H-NMR Spectra (CD$_3$OD, 500 MHz): δ3.28 (3H, s), 3.51 (1H, dt, J=2.4 and 4.8 Hz), 3.57 (3H, s), 3.63 (1H, d, J=4.8 Hz), 4.68 (1H, t, J=2.4 Hz), 6.68 (1H, t, J=2.4 Hz), 6.91 (1H, dd, J=0.4 and 8.4 Hz), 6.93 (1H, dt, J=0.4 and 7.8 Hz), 7.36 (1H, dt, J=2.0 and 7.8 Hz), 7.94 (1H, dd, J=2.0 and 7.8 Hz).

EXAMPLE 7

Synthesis of DHM3EQ 3,3-dimethoxy-4,5-epoxy-6-hydroxy-2-salicyloylamino-cyclohexene (87.0 mg, 0.283 mmol) was dissolved in acetone (2 ml), p-toluenesulfonic acid (5 mg) was added thereto and the mixture was stirred at room temperature for 1 hour. Ethyl acetate (20 ml) was added to the reaction mixture and the reaction mixture was washed with water (15 ml). After drying it over Glauber's salt, the ethyl acetate layer was concentrated under reduced pressure to obtain white solids, which were suspended in with ethyl acetate (1 ml) and stirred to wash them to obtain DHM3EQ (55.1 mg) as white solids (yield: 74%).

Appearance and Property: White powder, weakly acidic substance

Melting point: 178–182° C.,

Rf value of TLC: 0.36. (measured after development by thin layer chromatography silica gel (Art. 1.05715, produced by Merck, Inc.) with chloroform-methanol (10:1) as a development solvent, Infrared Absorption Spectra: νmax (KBr) 3457, 3102, 1696, 1620, 1559, 1381, 1233 cm$^{-1}$, Ultraviolet Absorption Spectra: λmax (MeOH) nm (ε) 248 (12000), 301 (9360), FAB Mass Spectrum (m/z): 262 (M+H)$^+$, Molecular formula: C$_{13}$H$_{11}$NO$_5$, $^1$H-NMR Spectra(DMSO-d$_6$, 400 MHz): δ3.63 (1H, d, J=3.9 Hz), 3.84 (1H, br), 4.87 (1H, br s), 6.97 (2H, overlapped), 7.42 (2H, overlapped), 7.94 (1H, d, J=8.0 Hz), 10.60 (1H, br s), 11.71 (1H, br s).

What is claimed is:
1. Salicylamide derivatives represented by formula (1)

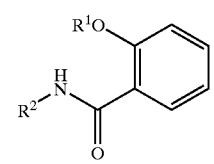

(1)

wherein R$^1$ represents a hydrogen atom or a C2–4 alkanoyl group, R$^2$ represents a group represented by the following formulae (A), (B), (C), (D), (E), (F) or (G):

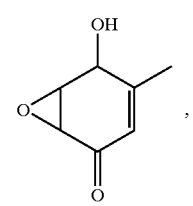

(A)

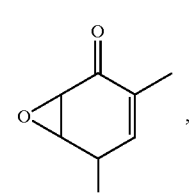

(B)

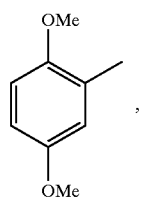

(C)

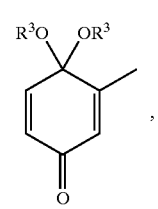

(D)

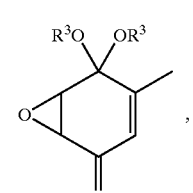

(E)

-continued (F)
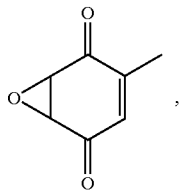

(G)
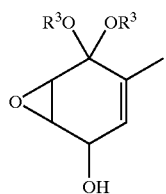

wherein R³ represents a C1–4 alkyl group.

2. Salicylamide derivatives as claimed in claim 1, represented by formulae (1a) or (1b)

(1a)
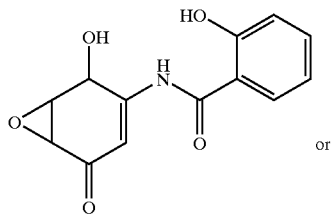

or (1b)
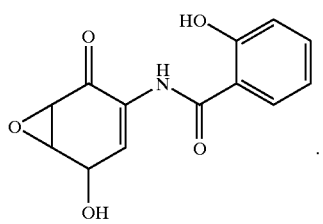

3. Salicylamide derivatives as claimed in claim 1, represented by formula (2)

(2)
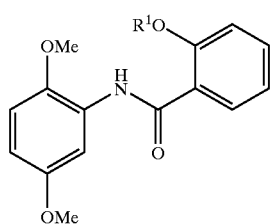

wherein the symbol in the formula has the same meaning as described in claim 1.

4. Salicylamide derivatives as claimed in claim 1, represented by formula (3)

(3)
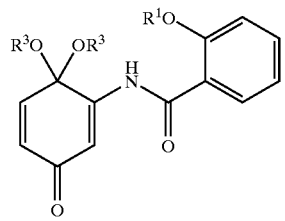

wherein the symbols in the formula have the same meanings as described in claim 1.

5. Salicylamide derivatives as claimed in claim 1, represented by formula (4)

(4)
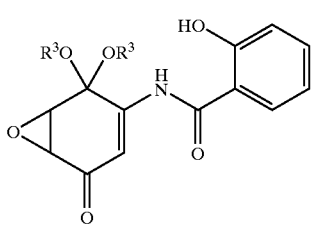

wherein the symbol in the formula has the same meaning as descrobed in claim 1.

6. A salicylamide derivative as claimed in claim 1, represented by formula (5)

(5)
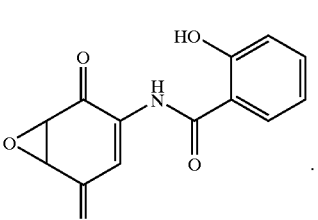

7. Salicylamide derivatives as claimed in claim 1, represented by formula (6)

(6)
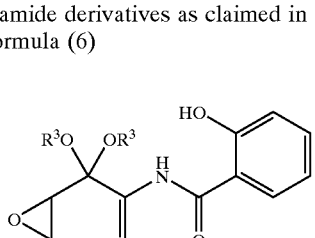

wherein the symbol in the formula has the same meaning as described in claim 1.

8. A process for producing salicylamide derivatives represented by formula (2)

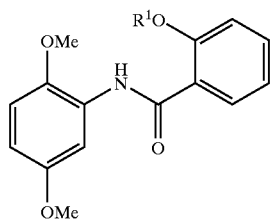

(2)

wherein the symbol in the formula has the same meaning as in described above, comprising reacting 2,5-dimethoxyaniline with O-alkanoylsalicyloyl halide represented by formula (7)

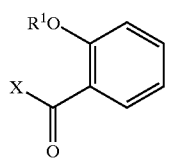

(7)

wherein $R^1$ has the same meaning as described in claim 1, and X represents a halogen atom.

9. A process for producing salicylamide derivatives represented by formula (3)

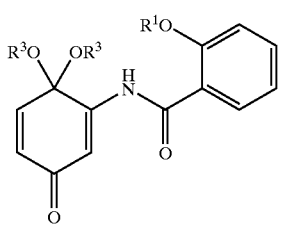

(3)

wherein the symbols in the formula have the same meanings as described above, comprising reacting a salicylamide derivative represented by formula (2)

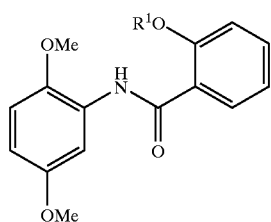

(2)

wherein the symbol in the formula has the same meaning as described in claim 1, with an alkanol represented by formula $R^3OH$ wherein $R^3$ is a C1–4 alkyl group, in the presence of a compound represented by a formula $C_6H_3I(OAc)_2$ wherein Ac is an acetyl group.

10. A process for producing salicylamide derivatives represented by formula (4)

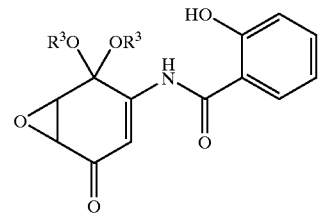

(4)

wherein the symbol in the formula has the same meaning as described above, comprising subjecting a salicylamide derivative represented by formula (3)

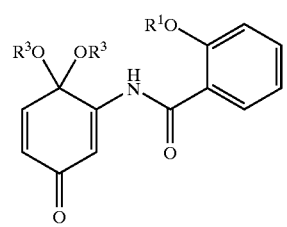

(3)

wherein the symbols in the formula have the same meanings as described in claim 1, to epoxidation.

11. A process for producing a salicylamide derivative represented by formula (5)

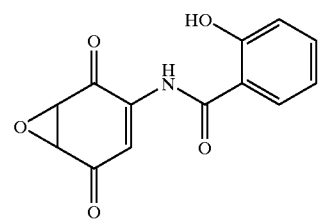

(5)

comprising subjecting a salicylamide derivative represented by formula (4)

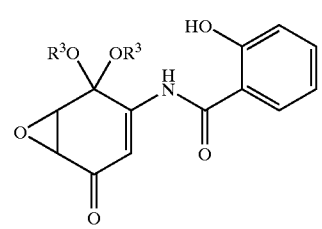

(4)

wherein the symbols in the formula have the same meanings as described in claim 1, to dedialkylketalation.

12. A process for producing salicylamide derivatives represented by formula (6)

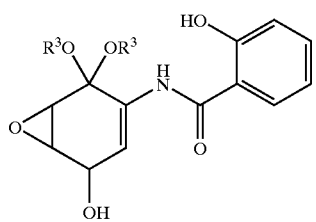

(6)

wherein the symbol in the formula has the same meaning as described above, comprising subjecting a salicylamide derivatives represented by formula (4)

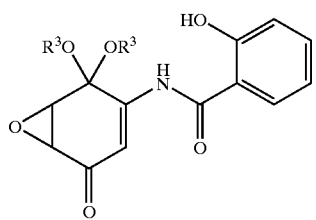

(4)

wherein the symbols in the formula have the same meanings as described in claim 1, to reduction.

13. A process for producing a salicylamide derivative represented by formula (1a)

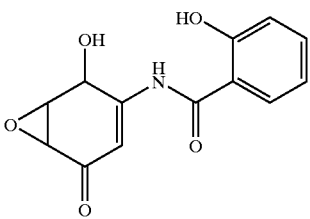

(1a)

comprising subjecting a salicylamide derivative represented by formula (5)

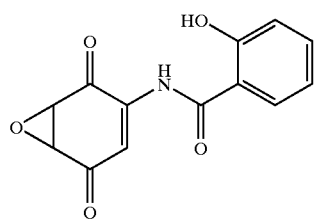

(5)

to reduction.

14. A process for producing a salicylamide derivative represented by formula (1b)

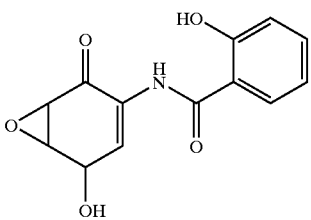

(1b)

comprising subjecting a salicylamide derivative represented by formula (6)

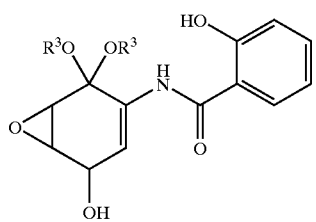

(6)

wherein the symbol in the formula has the same meaning as described in claim 1, to dedialkylketalation.

15. A drug comprising a salicylamide derivative represented by formulae (1a) or (1b) as claimed in claim 2 or a salt thereof as the active ingredient.

16. An agent for inhibiting the activation of NF-κB comprising a salicylamide derivative represented by formulae (1a) or (1b) as described in claim 2 or a salt thereof as the active ingredient.

17. Anti-inflammatory agent or immunosuppressive agent, comprising a salicylamide derivative represented by formulae (1a) or (1b) as described in claim 2 or a salt thereof as the active ingredient.

* * * * *

UNITED STATES PATENT AND TRADEMARK OFFICE
CERTIFICATE OF CORRECTION

PATENT NO. : 6,566,394 B1
DATED : May 20, 2003
INVENTOR(S) : Takeuchi et al.

It is certified that error appears in the above-identified patent and that said Letters Patent is hereby corrected as shown below:

Column 20,
Line 32, "descrobed" should read -- described --.

Column 21,
Line 14, before "described", delete "in".

Column 23,
Line 16, "derivatives" should read -- derivative --.

Signed and Sealed this

Sixteenth Day of September, 2003

JAMES E. ROGAN
*Director of the United States Patent and Trademark Office*